US010386509B2

(12) United States Patent
Chen et al.

(10) Patent No.: US 10,386,509 B2
(45) Date of Patent: Aug. 20, 2019

(54) RAY ENERGY CALIBRATION DEVICE, RAY ENERGY CALIBRATION METHOD AND RAY IMAGING SYSTEM

(71) Applicant: Nuctech Company Limited, Beijing (CN)

(72) Inventors: Yumei Chen, Beijing (CN); Xinshui Yan, Beijing (CN); Quanwei Song, Beijing (CN); Wei Yin, Beijing (CN); Weiqiang Guan, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 16/135,873

(22) Filed: Sep. 19, 2018

(65) Prior Publication Data

US 2019/0033475 A1 Jan. 31, 2019

(30) Foreign Application Priority Data

Sep. 19, 2017 (CN) .......................... 2017 1 0850203

(51) Int. Cl.
*G01T 7/00* (2006.01)
*A61B 5/107* (2006.01)
*A61B 6/00* (2006.01)

(52) U.S. Cl.
CPC ............ *G01T 7/005* (2013.01); *A61B 5/1075* (2013.01); *A61B 6/58* (2013.01); *A61B 6/585* (2013.01)

(58) Field of Classification Search
CPC ......... A61B 5/1075; A61B 6/58; A61B 6/582; A61B 6/585; G01T 7/005
See application file for complete search history.

(56) References Cited

U.S. PATENT DOCUMENTS

| 5,561,290 | A | * | 10/1996 | Strobel | ..................... | G01J 1/02 |
| | | | | | | 250/252.1 |
| 2010/0296631 | A1 | * | 11/2010 | Gillett | ..................... | G21K 1/043 |
| | | | | | | 378/150 |
| 2013/0043390 | A1 | * | 2/2013 | De Ruyter | ............ | G01J 1/0295 |
| | | | | | | 250/338.1 |

(Continued)

FOREIGN PATENT DOCUMENTS

CN   204495742 U   7/2015
CN   205729382 U   11/2016

OTHER PUBLICATIONS

Extended European Search Report for International Application No. 18195278.9 dated Mar. 8, 2019, which corresponds in priority to the above-identified subject U.S. Application.

*Primary Examiner* — Mark R Gaworecki
(74) *Attorney, Agent, or Firm* — Knobbe, Martens, Olson & Bear, LLP

(57) ABSTRACT

The disclosed technology relates to a ray energy calibration device and method, and a ray imaging system. In one aspect, the ray energy calibration device includes a plurality of wheels arranged to rotatable about a common shaft and each provided with one or more protruding blocks at respective specific positions of an outer circumference thereof. The ray energy calibration device further includes a plurality of calibration members, with each of the calibration members being configured such that through rotation of a corresponding one of the wheels, the calibration member can be moved to a calibration position by the protruding block at a specific position on the outer circumference of the wheel.

14 Claims, 3 Drawing Sheets

(56) References Cited

U.S. PATENT DOCUMENTS

| | | | | |
|---|---|---|---|---|
| 2014/0309959 A1* | 10/2014 | Shen | ............... | G01N 33/241 |
| | | | | 702/100 |
| 2017/0184513 A1* | 6/2017 | Chen | ............... | G01N 23/04 |
| 2017/0269260 A1* | 9/2017 | Chen | ............... | G01V 13/00 |

* cited by examiner

US 10,386,509 B2

RAY ENERGY CALIBRATION DEVICE, RAY ENERGY CALIBRATION METHOD AND RAY IMAGING SYSTEM

CROSS-REFERENCE TO RELATED APPLICATIONS

This application claims priority to Chinese Patent App. No. 201710850203.3, which was filed on Sep. 19, 2017 and which is hereby incorporated by reference in its entirety.

BACKGROUND OF THE DISCLOSED TECHNOLOGY

Field of the Technology

The disclosed technology relates to the field of non-destructive ray inspection, and in particular, to a ray energy calibration device and a ray energy calibration method for use in a high energy X-ray imaging inspection system.

Description of the Related Technology

During ray imaging, the capability of penetrating through matter often needs to be calibrated and adjusted properly so as to obtain an appropriate inspection image. A calibration device is placed between a ray source and a detector, and an existing calibration member comprises a collimation plate and a plurality of calibration parts, and thus, has a large volume and weight due to its configuration.

With the wide applications of vehicle-carried container inspection systems and requirements for calibrating a number of objects, it is desired that the calibration device is made more compact and integrated with an accelerator. This requires that an energy calibration device has a compact structure, occupies a small space, and has a lighter total weight.

SUMMARY OF CERTAIN INVENTIVE ASPECTS

The disclosed technology provides a ray energy calibration device and a ray energy calibration method, which can at least solve the problem of a rather large volume in prior art apparatus, and enable fast alignment between a ray beam from the inspection system and a detector module.

In an aspect of the disclosed technology, there is provided a ray energy calibration device, comprising: a plurality of calibration members configured to enter a ray region, through which rays pass, so as to calibrate energies of the rays; and a plurality of wheels arranged to be synchronously rotatable about a common shaft and each provided with one or more protruding blocks at respective specific positions of an outer circumference thereof, the plurality of wheels being arranged such that the calibration members are respectively driven by each of the one or more protruding blocks of the wheels for one or more times during one circle of rotation of the wheels, at least one of the wheels being provided with a plurality of protruding blocks on outer circumferences thereof; wherein, each of the calibration members is arranged to correspond to one of the plurality of wheels, such that the protruding blocks at respective specific position of the outer circumference of each of the plurality of wheels is movable, through rotation of a corresponding one of the plurality of wheels, from a position where the protruding blocks are not in contact with the calibration members to a position where the protruding blocks are in contact with the calibration members, so as to respectively drive the calibration members to move from initial positions to calibration positions in a radial direction of the wheel and away from the outer circumference of the wheel; and wherein each of the plurality of wheels is rotatable such that the one or more protruding blocks thereon moves away from the position where the protruding blocks are in contact with the calibration members to disengage with the calibration members, so that the calibration members return to the initial positions from the calibration positions.

In one embodiment of the disclosed technology, the one or more protruding blocks of each of the plurality of wheels are discretely distributed to drive the calibration members several times during one circle of simultaneous rotation of the wheels.

In one embodiment of the disclosed technology, the one or more protruding blocks of each of the plurality of wheels are arranged such that during one circle of rotation of the shaft, the one or more protruding blocks of each of the plurality of wheels drives corresponding calibration members to move, and the moved calibration members form a plurality of combinations of calibration members for calibrating a plurality of predefined values of ray energies.

In one embodiment of the disclosed technology, the one or more protruding blocks are shaped to be adapted to gradually push corresponding calibration members with rotation of the wheel on which the protruding blocks are mounted.

In one embodiment of the disclosed technology, the ray energy calibration device further comprises a plurality of restoration members each configured to provide a restoring force to a corresponding one of the calibration members such that the corresponding calibration member is allowed to return to the initial position from the calibration position.

In one embodiment of the disclosed technology, the calibration members each further comprises a calibration member base, the calibration blocks are each mounted on one side of the calibration member base, and the calibration members each comprises a contact part provided on the other side of the calibration member base for contact with a corresponding one of the protruding blocks, such that with rotation of the wheel, the protruding block becomes to contact the contact part and subsequently push the calibration member base to move.

In one embodiment of the disclosed technology, the contact part has a contact pulley configured to be rotatable in a state where the protruding block is in contact with the contact part.

In one embodiment of the disclosed technology, the ray energy calibration device further comprises a first bracket on which the shaft is mounted, and the first bracket comprises a first shielding part configured to block rays within the ray energy calibration device from leaking out of the ray energy calibration device.

In one embodiment of the disclosed technology, the ray energy calibration device further comprises a second bracket on which the one or more calibration members are mounted, and the second bracket comprises one or more sliding grooves, through which calibration blocks of the calibration members are guided to enter the ray region.

In one embodiment of the disclosed technology, the ray energy calibration device further comprises a second shielding part provided on the second bracket to block rays in the ray region from leaking and entering the ray energy calibration device, and the second shielding part and the first shielding part are located within planes perpendicular to each other.

In one embodiment of the disclosed technology, the ray energy calibration device further comprises a motor configured to drive the shaft to rotate, and a driving belt for connecting the motor and the shaft so as to drive the shaft by a driving force from the motor.

In another aspect, there is provided a ray energy calibration method for calibrating rays by using the ray energy calibration device as described above, the method comprising: determining a calibration thickness; rotating the shaft by an angle such that one or more of the calibration members enters the ray region; and adjusting energies of the rays based on the calibration thickness.

In one embodiment of the disclosed technology, the method further comprises: determining a plurality of calibration thicknesses according to actual requirements; and performing calibration for the plurality of calibration thicknesses by arranging and combining a plurality of calibration blocks; wherein when the shaft is rotated, some of the calibration blocks are pressed by the protruding blocks on corresponding ones of the wheels into the ray region, while others of the calibration blocks are not pressed into the ray region due to not in contact with the protruding blocks on corresponding ones of the wheels, so that the calibration block pressed into the ray region form a plurality of combinations of the calibration thicknesses.

In a further aspect, there is provided a ray imaging system, comprising the ray energy calibration device as described above.

In the ray energy calibration device of the disclosed technology, a plurality of calibration members may be integrated together, and each wheel comprises a plurality of protruding blocks, so that multiple levels of energies can be calibrated by several wheels, and a compact structure may be provided for use in a vehicle-carried inspection system, thereby having a better commercial value.

DETAILED DESCRIPTION OF CERTAIN ILLUSTRATIVE EMBODIMENTS

Figure 1:
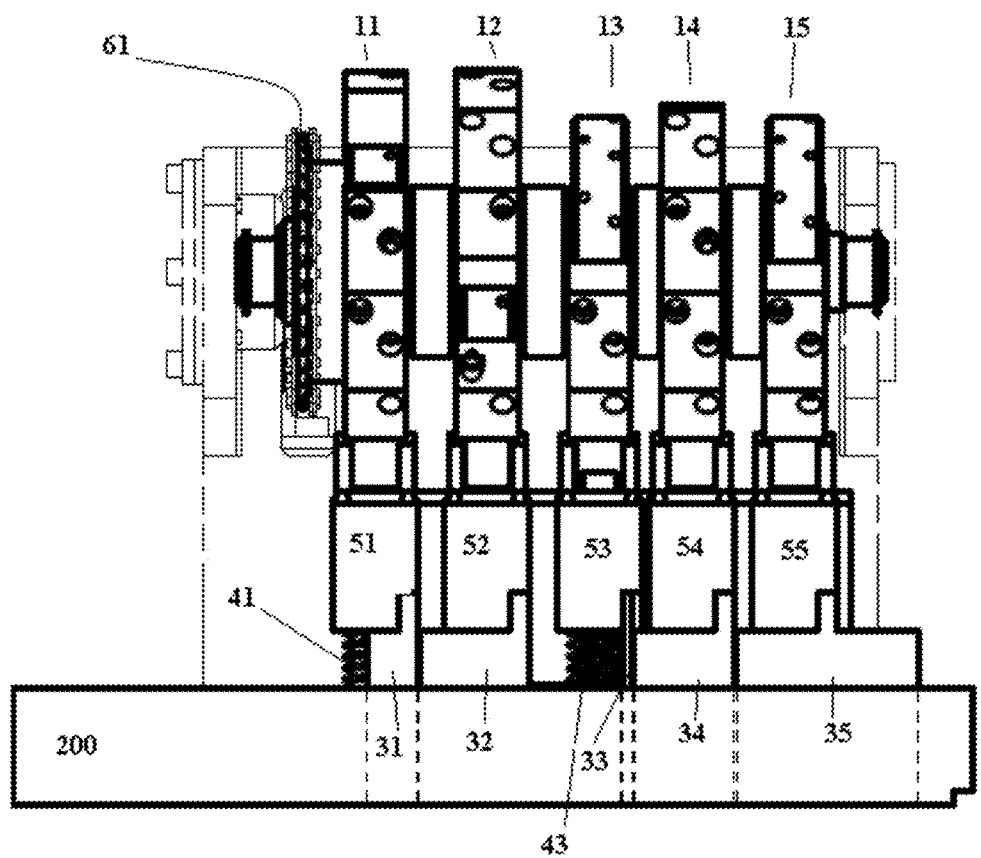
FIG. 1 is a side view schematically showing a ray energy calibration device according to an embodiment of the disclosed technology.

The disclosed technology will be described further hereinafter in detail with reference to the embodiments in combination with attached drawings. Further, in the following description, the likes or corresponding members or structures are denoted by the like reference numerals and repeated description thereof will be omitted.

As shown in FIG. 1, an embodiment of the disclosed technology provides a ray energy calibration device. The ray energy calibration device comprises a plurality of wheels 11, 12, 13, 14 and 15 arranged to be rotatable about a common shaft and each provided with one or more protruding blocks at respective specific positions of an outer circumference thereof, for example, a protruding block 21 on the wheel 11, a protruding block 22 on the wheel 12, a protruding block 23 on the wheel 13, a protruding block 24 on the wheel 14, and a protruding block 25 on the wheel 15. In an example, at least one of the wheels is provided with a plurality of protruding blocks on outer circumferences thereof. In one embodiment, for example, the wheel 11 is provided with a plurality of protruding blocks, which are discretely distributed on the wheel 11, in other words, the protruding blocks may be distributed at an interval, or two protruding blocks may be arranged closely adjacent to each other. In one embodiment of the disclosed technology, the ray energy calibration device comprises five wheels 11, 12, 13, 14 and 15, as shown in FIG. 1, and each wheel is provided with one or more protruding blocks, for example, the wheels 11, 12, 13 and 14 each have a plurality of protruding blocks. The number of the protruding blocks and respective positions of the protruding blocks on the outer circumference of the wheels may be set as required, and the number of the protruding blocks shown in the drawings of the present application is only intended to illustrate possible set positions of the protruding blocks and are not intended to limit the mounting number and positions of the protruding blocks.

Ray energy calibration device further comprises a plurality of calibration members. In the device shown in FIG. 3, the calibration members include calibration blocks 31, 32, 33, 34 and 35. In other embodiments of the disclosed technology, the calibration members are directed of related parts for calibration. The calibration members each include one calibration block 31, 32, 33, 34 and 35, a calibration member base with one calibration block mounted thereon, a restoration member and the like. When it is described that the calibration member is driven by the protruding block, it means that the whole calibration member is moved, such that the calibration block of the calibration member enters the ray region. However, the protruding block may be not in direct contact with the calibration block, and rather, may contact other part of the calibration member so as to move the calibration member. The calibration member may also be a one-piece part, thus the calibration member may also be regarded as a calibration block. The calibration blocks 31, 32, 33, 34 and 35 are arranged to enter a ray region 200, through which rays pass, so as to calibrate energies of the rays. Each wheel corresponds to one calibration member, for example, the wheel 11 corresponds to the calibration member 31. In the embodiment shown in FIG. 1, the ray energy calibration device has five calibration blocks 31, 32, 33, 34 and 35. Size (for example, thickness) and material of each of the calibration blocks 31, 32, 33, 34 and 35 may be preset as desired.

It is advantageous that a plurality of protruding blocks are provided on the outer circumference of one wheel, so that a corresponding one of the calibration members may be driven by the protruding blocks on the one wheel for several times during one circle of rotation of the one wheel. In other words, a plurality of protruding blocks are arranged at a plurality of positions, such that during one circle of rotation of the wheels, the calibration members may be driven by the protruding blocks at a plurality of predetermined rotation positions to enable calibration. In other words, several calibration operations may be performed by one wheel upon one circle of rotation of the wheel. With such configuration, the number of the wheels for carrying thereon the protruding blocks is greatly reduced, and thus the volume and mechanical complexity of the whole device are reduced.

With rotation, the one or more protruding blocks at specific positions on the outer circumference of each wheel may be moved from positions where they are not in contact with the calibration members to positions where they are in contact with the calibration members, so as to drive the calibration members to move away from initial positions to calibration positions in a radial direction of the wheel, i.e., in a direction towards away from the outer circumference of the wheel. In the drawings of the disclosed technology, the protruding block presses down the calibration member in a downward direction. With rotation of the wheels, each wheel may be rotated such the protruding block on the each wheel leave away from the calibration members, thereby the calibration members return to the initial positions from the calibration positions.

Figure 2:
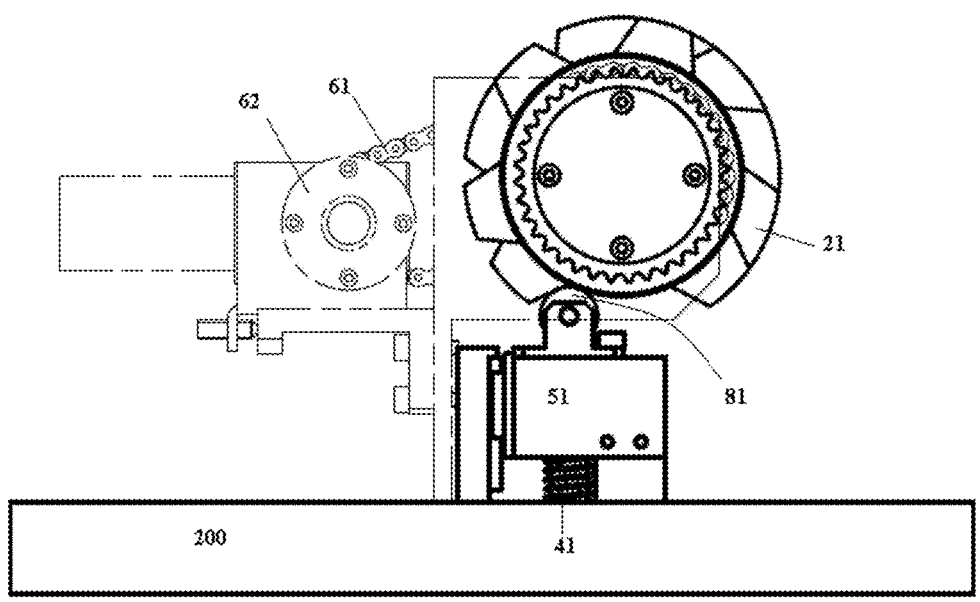
FIG. 2 is a front view schematically showing a ray energy calibration device according to an embodiment of the disclosed technology.

In one embodiment of the disclosed technology, the ray energy calibration device further comprises a plurality of restoration members each corresponding to one of the calibration members. Each restoration member is configured to provide a restoring force to the corresponding one of the calibration members such that the corresponding calibration member is allowed to return to the initial position from the calibration position. For example, in the configuration shown in FIGS. 1-3, the restoration members may include restoration springs 41, 42, 43, 44 and 45, and each restoration member is connected with a corresponding one of the calibration members. FIG. 2 shows that the wheel 11 corresponds to the calibration member (51, indicates a part of the calibration member in contact with the restoration spring), and the calibration member corresponds to the restoration spring 41; similarly, the wheel 13 corresponds to the calibration member (53, indicates a part of the calibration member in contact with the restoration spring), and the calibration member 53 corresponds to the restoration spring 43. When one calibration member is driven by the protruding block on the outer circumference of the wheel corresponding to the one calibration member, the one calibration member is pressed downward by the protruding block, and the restoration spring 41 is compressed; after the protruding block leaves away, the compressed restoration spring 41 drives the calibration member upward to return to the initial position.

Figure 3:
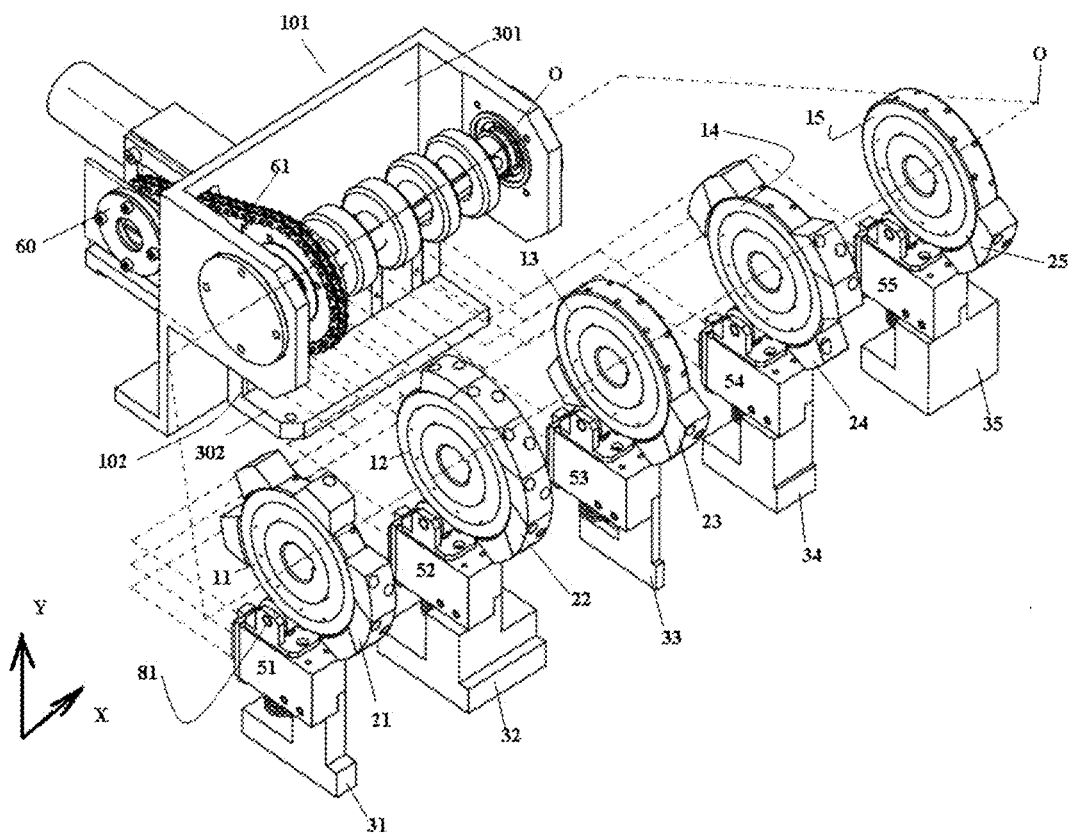
FIG. 3 is an exploded view schematically showing a ray energy calibration device according to an embodiment of the disclosed technology, where wheels and corresponding calibration members are detached from the ray energy calibration device.

In one embodiment of the disclosed technology, the plurality of wheels 11, 12, 13, 14 and 15 are mounted on and driven by a common shaft O so as to be synchronously rotated. The ray energy calibration device may further comprise a motor 60, as shown in FIG. 3, configured to drive the shaft O to rotate. Such arrangement allows to use one motor 60 to drive the entire plurality of wheels 11, 12, 13, 14 and 15, so the whole device is simpler in structure. Further, in such arrangement, calibration of a desired calibration thickness may be still achieved by setting the number of the protruding blocks and positions thereof on the outer circumferences of respective wheels.

In this embodiment, the motor 60 may drive the shaft O to rotate by means of such as a belt, a chain 61 or a gear transmission mechanism. For example, a driving wheel may be provided onto the shaft O, and the motor 60 may drive the driving wheel and thus the shaft O to rotate by means of, for example, a driving belt such as a belt or chain 61, so that all wheels 11, 12, 13, 14 and 15 mounted on the shaft O are rotated along with the rotation of the shaft. Since only one driving belt is used, only one opening is required for the driving belt, thereby reducing risk of radiation leakage.

In one embodiment, one or more protruding blocks on each of the plurality of wheels are arranged such that during one circle of rotation of the shaft O, the one or more protruding blocks of each of the plurality of wheels 11, 12, 13, 14 and 15 may drive corresponding calibration members to move, and the moved calibration members may form a plurality of combinations of calibration members for calibrating a plurality of predefined ray energies. In the following, a calibration operation will be described by taking five wheels 11, 12, 13, 14 and 15 and calibration blocks 31, 32, 33, 34 and 35 of five corresponding calibration members as an example.

It is noted that in theory, one calibration member may achieve calibration of time of $C_1^1=1$ thickness; two calibration members may achieve calibration of times of $C_2^1+C_2^2=3$ thicknesses through combinations thereof; three calibration members may achieve calibration of times of $C_3^1+C_3^2+C_3^3=7$ thicknesses through combinations thereof; four calibration members may achieve calibration of times of $C_4^1+C_4^2+C_4^3+C_4^4=15$ thicknesses through combinations thereof, and so on. In practice, however, it is not necessary to utilize all of the combinations of all calibration members, and some desired combinations may be selected according to actual conditions. The following table gives five calibration members and sizes thereof, and calibration thicknesses which may be at least calibrated in practice through these five calibration members.

| calibration thickness | Sizes of calibration members corresponding to respective wheels (unit: mm) | | | | |
|---|---|---|---|---|---|
| | first wheel: 5 | second wheel: 12.7 | third wheel: 25.4 | fourth wheel: 45.8 | fifth wheel: 50.8 |
| 5 | ✓ | | | | |
| 12.7 | | ✓ | | | |
| 25.4 | | | ✓ | | |
| 38.1 | | ✓ | ✓ | | |
| 50.8 | | | | | ✓ |
| 63.5 | | ✓ | | | ✓ |
| 76.2 | | | ✓ | | ✓ |
| 88.9 | | ✓ | ✓ | | ✓ |
| 114.3 | ✓ | ✓ | | ✓ | ✓ |
| 139.7 | ✓ | ✓ | ✓ | ✓ | ✓ |

In the above example table, symbol ✓ means a calibration member for calibrating a desired calibration thickness in practice. As can be seen, the five calibration members may calibrate at least ten calibration thicknesses commonly used in practice. Technique solutions of the disclosed technology are of positive guidance significance in practice applications, because it is not required that the number of the calibration thicknesses is infinite, but rather a limited number of calibration thicknesses may meet actual application requirements within certain application ranges, thus a plurality of combinations of calibrations implemented by a few calibration blocks may satisfy actual application requirements.

Particularly, in one application, thicknesses of calibration members corresponding to the five wheels 11, 12, 13, 14 and 15 are 5 mm, 12.7 mm, 25.4 mm, 45.8 mm and 50.8 mm respectively. When the calibration thickness is 5 mm, the five wheels 11, 12, 13, 14 and 15 are rotated, so that the protruding blocks on the first wheel 11 begin to push the corresponding calibration block to move to the ray region 200, while protruding blocks on other wheels 12, 13, 14 and 15 are not moved to positions where they may contact and push corresponding calibration members, thereby the calibration member corresponding to the first wheel 11 implements the calibration operation.

Similarly, when the wheels continue to be rotated, for example, only the protruding blocks on the second wheel 12 and the third wheel 13 push corresponding calibration members, and the protruding blocks on the outer circumferences of other wheels 11, 14 and 15 do contact the calibration members. At this time, the calibration blocks corresponding to the second wheel 12 and the third wheel 13 together achieve calibration thickness of 12.7 mm+25.4 mm=38.1 mm. When the wheels continue to rotate, the protruding blocks on the second wheel 12 and the third wheel 13 leave away again, thereby corresponding calibration members return to the initial positions from the calibration positions.

Similar operations may be made for obtaining other calibration thicknesses, and will not be repeatedly described.

As such, during one circle of rotation of each wheel, one or more protruding blocks on the wheel will drive calibration members for one or more times. For example, in the configuration shown in FIGS. 1-3, there are six protruding blocks on the outer circumference of the wheel 11, so that during one circle of rotation of the wheel 11, the six protruding blocks will each be brought to contact the calibration members for one time respectively, thereby the calibration members are pressed down by six times. As can be seen from FIG. 3, sizes of all protruding blocks on the five wheels 11, 12, 13, 14 and 15 are approximately the same, in other words, the thicknesses of the protruding blocks in the radial direction of the wheel are the same and arc lengths of the outer circumferences of the protruding blocks are approximately the same. As such, when the wheel is rotated by an angle, all of the protruding blocks that have been in contact with the calibration member will leave away from the calibration member at the same time. In FIG. 3, three protruding blocks on the outer circumference of the wheel 11 adjoin to each other; as such, when the wheel is rotated and after the first protruding block leaves away from the calibration member, the second protruding block continuously contacts the calibration member; further, after the wheel continues to be rotated by a same angle, the second protruding block leaves away from calibration member, and the third protruding block continuously contacts the calibration member; after the wheel continues to be rotated by a same angle, the third protruding block leaves away from calibration member. During the above entire rotation of the wheel, the three protruding blocks maintain the calibration member to be in calibration position.

According to an embodiment of the disclosed technology, positions of the protruding blocks on the outer circumferences of the five wheels 11, 12, 13, 14 and 15 are fixed respectively, and are arranged such that desired calibration thicknesses are obtained by loading the calibration members into calibration positions by corresponding protruding blocks on the wheels 11, 12, 13, 14 and 15 during rotations of the wheels 11, 12, 13, 14 and 15, and one calibration thickness is obtained by calibration blocks that are pressed down by one or more protruding blocks. The above table shows calibration thicknesses desired in practice applications. As can be seen, in embodiments of the disclosed technology, five calibration members may achieve ten calibration thicknesses, thus the number of the corresponding wheels may be reduced while achieve a same number of calibration thicknesses, thereby reducing complexity and volume of the calibration device.

In an embodiment of the disclosed technology, the protruding blocks are shaped to be adapted to gradually push corresponding calibration members with rotation of the wheel on which the protruding blocks are mounted. For example, a side face of the protruding block may be an inclined or arced face, so that when the wheel is rotated, the protruding block is moved circumferentially along with the rotation of the wheel, and the side face of the protruding block firstly contacts a top of the calibration member; the inclined or arced face facilitates reduction of friction between the side face of the protruding block and the top of the calibration member, so that it is easier for the protruding block to continue to rotate until the outer circumference of the protruding block contacts the top of the calibration member. As such, the calibration member is pressed down.

In one embodiment, the calibration members may comprise calibration member bases 51, 52, 53, 54 and 55 respectively, the calibration blocks of the calibration member are mounted on one side of the calibration member base, and the calibration members each comprises a contact part provided on the other side of the calibration member base for contact with a corresponding one of the protruding blocks, such that with circumferential rotation movement of the wheel, the protruding blocks becomes to contact the contact part and subsequently push the calibration member base to move.

The contact parts may each have or may be contact pulleys 81, 82, 83, 84 and 85 respectively, which facilitate, when the contact pulleys 81, 82, 83, 84 and 85 are in contact with the protruding blocks, reduction in contact friction through rotation. The arrangement of the contact pulleys 81, 82, 83, 84, 85 is advantageous. The rotatable contact pulleys 81, 82, 83, 84, 85 are arranged on the top of the calibration member bases, so that circumferential movement of the protruding block may be transformed into linear movement of the whole calibration member base, that is, linear movement of the calibration member (a downward movement shown in FIG. 3), through contact between the contact pulleys and the protruding block. Since contact pulley may provide reduced friction and may slide smoothly and stably, the stability of operation of the device is improved, and service life of the calibration member base and the protruding block are increased.

In the embodiment shown in FIG. 3, each calibration member may comprise a corresponding calibration member base, and a contact part may be provided on a top of the calibration member base (as shown in the figure); the contact part may be a contact pulley 81, 82, 83, 84 or 85. A corresponding calibration block is arranged under the calibration member base (as shown in the figure). In the embodiment shown in FIG. 3, thicknesses of the calibration blocks may be 5 mm, 12.7 mm, 25.4 mm, 45.8 mm and 50.8 mm respectively. However, the thicknesses of the calibration blocks may alternatively have other values, which may be set as required.

The calibration member base may be regarded as a part of the ray energy calibration device, or may be regarded as a part of the calibration member, which are only difference in description. For example, in one embodiment, the calibration member base may be omitted, and the calibration member is shaped such that its upper portion is provided with contact pulleys 81, 82, 83, 84, 85, and its lower portion is an integrally formed as a calibration block. Alternatively, in one embodiment, the calibration member is a one piece. When it is described in the disclosed technology that the calibration member is used for calibrating or is combined to form a calibration thickness, it means that the calibration block or a combination of the calibration blocks form a calibration thickness.

In the embodiment shown in FIG. 3, the ray energy calibration device may further comprise a first bracket 101, the shaft O is mounted on the first bracket 101 and the five wheels 11, 12, 13, 14 and 15 are mounted on the shaft O. A driving wheel is further provided on the shaft O, and is connected with the motor by a belt or chain such that the motor 60 drives the driving wheel and thus the shaft O to rotate.

In another embodiment according to the disclosed technology, the ray energy calibration device does not include the motor, rather, the shaft O is manually driven to rotate.

In one embodiment of the disclosed technology, there is further provided a second bracket 102, on which the calibration members corresponding to the plurality of wheels are mounted, the second bracket 102 is provided with one or more sliding grooves (not shown), and each calibration member corresponds to one sliding groove, such that the calibration member or the calibration block of the calibration member are driven respectively by the protruding block to pass through the sliding groove of the second bracket 102 to enter the ray region 200, for implementing calibration; when the protruding block leaves away, the calibration member or the calibration block of the calibration member is returned to the initial position under the action of the restoration spring 41, 42, 43, 44, 45. The sliding groove may be configured to guide the calibration member or the calibration block of the calibration member. The second bracket 102 further comprises a second shielding part 302 for shielding rays from the ray region 200 so as to separate the rays from the ray energy calibration device. One or more sliding grooves are provided in the second shielding part 302, and in this case, the second shielding part 302 constitutes a portion of the second bracket 102. Other portions of the second bracket 102 are not described in detail and may be set as required by those skilled in the art. In another embodiment of the disclosed technology, the second shielding part 302 may be a part which is separately provided and mounted on a side of the second bracket 102 facing the ray region. The second bracket 102 may be connected with the first bracket 101. In another embodiment of the disclosed technology, however, the second bracket 102 and the first bracket 101 are integrally formed, or in this embodiment, the ray calibration device comprises a one-piece bracket having a first portion 101 for mounting the shaft O and a second portion 102 for mounting the calibration member.

In one embodiment of the disclosed technology, there may include a plurality of shielding parts. For example, a second shielding part 302 is provided on the second portion 102 of the bracket or on the second bracket 102, for blocking rays from the ray region 200 from entering the ray energy calibration device. Meanwhile, a first shielding part 301 is provided on the first portion 101 of the bracket or on the first bracket, and configured to isolate the ray energy calibration device from a user so as to prevent rays which leak into the ray energy calibration device from leaking to the outside of the device. For example, the first shielding part 301 is arranged between the motor and the wheels shown in FIG. 3. The arrangement of the first shielding part 301 and the belt or chain is advantageous in that use of the driving arrangement of the belt in embodiments of the disclosed technology may reduce an opening area of the first shielding part 301, so there is nearly no opening in the first shielding part 301, so that the ray energy calibration device may be completely sealed and at least one side of the ray energy calibration device may be isolated, thereby the amount of leakage of rays is greatly reduced. Advantageously, the first shielding part 301 and the second shielding part 302 are arranged to cooperate with each other such that the first shielding part 301 extends in a first direction and the second shielding part 302 extends in a second direction. In the configuration shown in FIG. 3, the second shielding part 302 extends in a horizontal direction X (in an XZ plane perpendicular to XY plane), and the first shielding part 301 extends in a vertical direction Y (in an XY plane), such that the rays from the ray region 200 (located below the calibration blocks shown in the figure) are firstly shielded by the second shielding part 302, and only little rays leak into the ray energy calibration device; thereby the little rays leaking into the ray energy calibration device may be substantially blocked by the first shielding part 301.

The ray energy calibration device of the disclosed technology is provided with a plurality of shielding parts (the first shielding part 301, the second shielding part 302) located within plane perpendicular to each other, so that the safety of the device is significantly improved through shielding of rays by two shielding parts.

In one embodiment of the disclosed technology, there is provided a ray energy calibration method for calibrating rays by using the ray energy calibration device as described above. The ray energy calibration method comprises: firstly, determining a calibration thickness as required; rotating the shaft by an angle such that one or more of the calibration members enters the ray region 200; and adjusting energies of the rays based on the calibration thickness. In one embodiment, according to actual requirements, a plurality of calibration thicknesses, for example, the ten desired calibration thicknesses listed in the above, are determined, while there are five calibration blocks. The plurality of calibration thicknesses are calibrated through arrangement and combinations of a plurality of calibration blocks. For example, ten calibration thicknesses may be calibrated by five 5 calibration blocks. Each combination of the calibration blocks are pressed, during rotation of the shaft, into the ray region by the protruding block of the corresponding wheels, while other calibration blocks are not in contact with the protruding block of the corresponding wheels. For example, protruding blocks are arranged on the circumference of the wheel such that positions on the circumferences of the five wheels where protruding blocks are respectively arranged are aligned with one another in a length direction of the shaft, such that when the wheels are rotated, one combination of calibration blocks are pressed down by the protruding blocks of some of the wheels. When the wheels continue to be rotated, the set of protruding blocks leave away from the calibration blocks and the calibration blocks return to the initial positions; then another set of calibration blocks are pressed down by another corresponding combination of protruding blocks so as to calibrate another calibration thickness, and so on. During one circle of rotation of the wheels, ten combinations of the five protruding blocks may be obtained to press down some of, or the entirety of, five calibration blocks, providing ten calibration thicknesses.

In practice, for example, thicknesses of the calibration members corresponding to five wheels are 5 mm, 12.7 mm, 25.4 mm, 45.8 mm and 50.8 mm respectively. If a calibration thickness to be obtained is 76.2 mm, the five wheels 11, 12, 13, 14 and 15 are rotated, such that protruding block of the third wheel 13 presses corresponding calibration members or calibration blocks into the ray region 200, and meanwhile the fifth wheel 15 presses corresponding calibration members or calibration blocks into the ray region 200, so that a combined thickness formed by the calibration blocks is 76.2 mm; the energy of rays are adjusted under the calibration thickness of 76.2 mm; after calibration of energy of rays, the shaft is rotated, such that the protruding blocks leave away from the calibration members, and the calibration blocks return to respective initial positions; and calibration is completed.

Similar operation is done for other calibration thicknesses. As more calibration thicknesses may be calibrated by fewer calibration blocks, the volume of the device can be greatly reduced.

In the above embodiments, a central angle of 360 degrees of the wheel may be divided into ten sections, that is, the ray energy calibration device may calibrate one calibration thickness once the wheel is rotated by 36 degrees. The calibration thickness may be identified through degrees of the central angle, there simplifying operation.

An embodiment of the disclosed technology further provides a ray imaging system comprising the ray energy calibration device as described above. Since the ray energy calibration device may be integrated into the ray imaging system, the volume of the ray imaging system may be greatly reduced.

Although several exemplary embodiments of the disclosed technology have been shown and described, it would be appreciated by those skilled in the art that various changes or modifications may be made in form and detail in these embodiments without departing from the principles and spirit of the present invention, the scope of which is defined in the claims and their equivalents.

What is claimed is:

1. A ray energy calibration device, comprising:
    a plurality of calibration members each comprising a calibration block and configured to enter a ray region, through which rays pass, so as to calibrate energies of the rays; and
    a plurality of wheels arranged to be synchronously rotatable about a common shaft and each provided with one or more protruding blocks at respective specific positions of an outer circumference thereof, the plurality of wheels being arranged such that the calibration members are respectively driven by each of the one or more protruding blocks of the wheels for one or more times during one circle of rotation of the wheels, at least one of the wheels being provided with a plurality of protruding blocks on outer circumferences thereof;
    wherein, each of the calibration members is arranged to correspond to one of the plurality of wheels, such that the protruding blocks at respective specific positions of the outer circumference of each of the plurality of wheels is movable, through rotation of a corresponding one of the plurality of wheels, from a position where the protruding blocks are not in contact with the calibration members to a position where the protruding blocks are in contact with the calibration members, so as to respectively drive the calibration members to move from initial positions to calibration positions in a radial direction of the wheel and away from the outer circumference of the wheel; and
    wherein each of the plurality of wheels is rotatable such that the one or more protruding blocks thereon moves away from the position where the protruding blocks are in contact with the calibration members to disengage with the calibration members, so that the calibration members return to the initial positions from the calibration positions.

2. The ray energy calibration device according to claim 1, wherein the one or more protruding blocks of each of the plurality of wheels are discretely distributed to drive the calibration members several times during one circle of simultaneous rotation of the wheels.

3. The ray energy calibration device according to claim 2, further comprising:
    a motor configured to drive the shaft to rotate; and
    a driving belt for connecting the motor and the shaft so as to drive the shaft by a driving force from the motor.

4. The ray energy calibration device according to claim 1, wherein the one or more protruding blocks of each of the plurality of wheels are arranged such that during one circle of rotation of the shaft, the one or more protruding blocks of each of the plurality of wheels drives corresponding calibration members to move, and the moved calibration members form a plurality of combinations of calibration members for calibrating a plurality of predefined values of ray energies.

5. The ray energy calibration device according to claim 1, wherein the one or more protruding blocks are shaped to be adapted to gradually push corresponding calibration members with rotation of the wheel on which the protruding blocks are mounted.

6. The ray energy calibration device according to claim 1, further comprising a plurality of restoration members each configured to provide a restoring force to a corresponding one of the calibration members such that the corresponding calibration member is allowed to return to the initial position from the calibration position.

7. The ray energy calibration device according to claim 1, wherein the calibration members each comprise a calibration member base,
    wherein the calibration blocks are each mounted on one side of the calibration member base, and the calibration members each comprises a contact part provided on the other side of the calibration member base for contact with a corresponding one of the protruding blocks, such that with rotation of the wheel, the protruding block contacts the contact part and subsequently pushes the calibration member base to move.

8. The ray energy calibration device according to claim 7, wherein the contact part has a contact pulley configured to be rotatable in a state where the protruding block is in contact with the contact part.

9. The ray energy calibration device according to claim 1, further comprising a first bracket on which the shaft is mounted,
    wherein the first bracket comprises a first shielding part configured to block rays within the ray energy calibration device from leaking out of the ray energy calibration device.

10. The ray energy calibration device according to claim 9, further comprising a second bracket on which the one or more calibration members are mounted,
    wherein the second bracket comprises one or more sliding grooves, through which calibration blocks of the calibration members are guided to enter the ray region.

11. The ray energy calibration device according to claim 10, further comprising a second shielding part provided on the second bracket to block rays in the ray region from leaking and entering the ray energy calibration device;
    wherein the second shielding part and the first shielding part are located within planes perpendicular to each other.

12. A ray energy calibration method for calibrating rays by using the ray energy calibration device of claim 1, the method comprising:
    determining a calibration thickness;
    rotating the shaft by an angle such that one or more of the calibration members enters the ray region; and
    adjusting energies of the rays based on the calibration thickness.

13. The ray energy calibration method according to the claim 12, wherein the method further comprises:
    determining a plurality of calibration thicknesses according to actual requirements; and performing calibration for the plurality of calibration thicknesses by arranging and combining a plurality of calibration blocks;

wherein when the shaft is rotated, some of the calibration blocks are pressed by the protruding blocks on corresponding ones of the wheels into the ray region, while others of the calibration blocks are not pressed into the ray region due to not in contact with the protruding blocks on corresponding ones of the wheels, so that the calibration block pressed into the ray region form a plurality of combinations of the calibration thicknesses.

14. A ray imaging system, comprising the ray energy calibration device of claim 1.

* * * * *